United States Patent
Hellstrand et al.

(10) Patent No.: US 6,790,440 B2
(45) Date of Patent: Sep. 14, 2004

(54) METHODS AND COMPOSITIONS FOR PROMOTING THE MATURATION OF MONOCYTES

(75) Inventors: Kristoffer Hellstrand, Gothenburg (SE); Svante H. Hermodsson, Mölndal (SE); Kurt R. Gehlsen, Encinitas, CA (US)

(73) Assignee: Maxim Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/160,745

(22) Filed: May 30, 2002

(65) Prior Publication Data

US 2002/0182176 A1 Dec. 5, 2002

Related U.S. Application Data

(62) Division of application No. 09/974,410, filed on Oct. 9, 2001.
(60) Provisional application No. 60/240,299, filed on Oct. 12, 2000.

(51) Int. Cl.$^7$ .................. A61K 38/19; A61K 38/44; A61K 31/40; A61K 31/415; A61K 31/355
(52) U.S. Cl. ............. 424/85.1; 424/94.4; 514/400; 514/419; 514/458; 514/474; 514/725
(58) Field of Search ............... 424/85.1, 85.2, 424/94.4; 514/419, 400, 458, 474, 725, 351, 885; 530/351

(56) References Cited

U.S. PATENT DOCUMENTS

| | | | |
|---|---|---|---|
| 5,702,697 A | | 12/1997 | Zimmerman et al. |
| 5,849,589 A | * | 12/1998 | Tedder et al. .............. 435/377 |

FOREIGN PATENT DOCUMENTS

| | | | |
|---|---|---|---|
| EP | 0 808 897 A1 | | 11/1997 |
| WO | WO-96/05289 A1 | * | 2/1996 |
| WO | WO-97/42968 A2 | * | 11/1997 |
| WO | 99/51257 | | 10/1999 |
| WO | 00/10600 | | 3/2000 |
| WO | 00/40240 | | 7/2000 |

OTHER PUBLICATIONS

Hellstrand et al. (2001) Up–regulation of the CD86 co–stimulatory antigen on human monocytes by combined treatment with histamine dihydrochloride and granulocyte–macrophage colony–stimulating factor (GM–CSF). 42:330. XP–001069964.

Courtesy copy of PCT International Search Report dated May 14, 2002 in 2 pages.

Avigan, D. (1999) Dendritic cells: development, function and potential use for cancer immunotherapy. Blood Reviews. 13:51–64.

Bell et al. (1999) Dendritic cells. Advances in Immunology. 72:255–324.

Croft et al. (1997) Accessory molecule and costimulation requirements for CD4 T cell response. Critical Reviews in Immunology. 17:89–118.

Gieseler et al. (1998) In–Vitro differentiation of mature dendritic cells from human blood monocytes. Developmental Immunology. 6:25–39.

Hellstrand et al. (1994) Histaminergic regulation of NK cells. The Journal of Immunology. 153:4940–4947.

Kiertscher et al. (1996) Human CD14+ leukocytes acquire the phenotype and function of antigen–presenting dentritic cells when cultured in GM–CSF and IL–4. Journal of Leukocyte Biology. 59:208–218.

Lawson et al. (2000) Granulocyte–macrophage colony–stimulating factor: another cytokine with adjuvant therapeutic benefit in melanoma? Journal of Clinical Oncology. 18(8):1603–1605.

McCoy et al. (1999) The role of CTLA–4 in the regulation of T cell immune responses. Immunology and Cell Biology. 77:1–10.

Slavik et al. (1999) CD2/CTLA–4 and CD80/CD86 Families. Immunologic Research. 19(1):1–24.

Spitler et al. (2000) Adjuvant therapy of stage III and IV malignant melanoma using granulocyte–macrophage colony–stimulating factor. Journal of clinical Oncology. 18(8):1614–1621.

* cited by examiner

Primary Examiner—Gary Kunz
Assistant Examiner—Ruixiang Li
(74) Attorney, Agent, or Firm—Knobbe Martens Olson & Bear LLP

(57) ABSTRACT

Disclosed is a method of promoting the maturation of monocytes comprising the administration of a reactive oxygen species (ROS) inhibitor or scavenger and at least one monocyte maturation-promoting agent. A composition for promoting the maturation of monocytes is likewise disclosed. The pharmaceutical composition includes a compound effective to promote the maturation of monocytes and a ROS inhibitor or scavenger combined in a pharmaceutically acceptable carrier.

9 Claims, No Drawings

METHODS AND COMPOSITIONS FOR PROMOTING THE MATURATION OF MONOCYTES

RELATED APPLICATIONS

This application is a divisional application of U.S. patent application Ser. No. 09/974,410, filed on Oct. 9, 2001, which claims priority to Provisional Application No. 60/240,299 entitled METHODS AND COMPOSITIONS FOR PROMOTING THE MATURATION OF MONOCYTES filed on Oct. 12, 2000. The subject matter of the aforementioned provisional application is hereby incorporated by reference.

BACKGROUND OF THE INVENTION

1. Field of the Invention

The disclosed invention relates to compositions and methods for promoting the maturation of monocytes. More specifically, the disclosed invention relates to the treatment of subjects suffering from cancer or infections with one or more monocyte maturation-promoting compounds.

2. Description of the Related Art

Monocytes, macrophages, and dendritic cells are of primary importance in the immune defense system of the body, playing a central role in the induction of the acquired immune response through their capacity to present antigen and regulate the function of T-lymphocytes.

Monocytes are mononuclear phagocytic white blood cells derived from the myeloid stem cells. Monocytes circulate in the blood stream and then move into tissues, at which point they mature into macrophages. Monocytes and macrophages are one of the first lines of defense in the immune process. Mononuclear phagocytes function as accessory cells in the recognition and activation phases of adaptive immune responses. Their main functions are to display antigens in a form that can be recognized by T lymphocytes and to produce membrane and secreted proteins that serve as secondary signals for T cell activation. Some mononuclear phagocytes may differentiate into dendritic cells, which play important roles in the induction of T lymphocyte responses to protein antigens.

During development, circulating monocytes migrate into essentially all body organs to form macrophages where they show highly heterogeneous phenotypes and functions based on tissue localization. During the immune process, signals are delivered to the bone marrow which promote the proliferation and release of promonocytes into the circulation where they are known as monocytes.

Numerous compounds such as colony stimulating factors and certain cytokines have been shown to regulate the development of mononuclear phagocytes. Granulocyte-macrophage colony-stimulating factor (GM-CSF), for example, is a cytokine which induces the differentiation, proliferation, and activation of a variety of immunologically active cell populations. GM-CSF facilitates the development of cell-mediated immunity, and recent studies suggest that a critical event in this action of GM-CSF is to induce the differentiation of monocytes into dendritic cells, which are potent antigen-presenting cells (Bell, D. et al., *Adv Immunol,* 72:255–324 (1999); Avigan, D., *Blood Rev.,* 13:51–64 (2000)).

Because of the potency of compounds such as GM-CSF as immune adjuvants, particular interest has focused on their use to overcome the poor immunological response associated with cancer and chronic infections (for review, see Lawson, D., and Kirkwood, J. M., *J. Clin. Oncol.,* 18:1603–1605 (2000)). For example, treatment with GM-CSF has been proposed to protect a substantial fraction of patients with high-risk malignant melanoma against relapse and death. In a study by Spitlier and co-workers, the median survival time of GM-CSF-treated melanoma patients (with stage III or stage IV disease) was increased by a factor of three as compared with that of matched control patients (Spitlier et al., *J. Clin. Oncol.,* 18:1614–1621).

Despite these results, there is a need for improvement of monocyte maturation-promoting therapy in the treatment of neoplastic disease and chronic infections.

SUMMARY OF THE INVENTION

The disclosed invention relates to compositions and methods for promoting the maturation of monocytes. In one embodiment, a method for promoting the maturation of monocytes is provided. A composition including a reactive oxygen species (ROS) inhibiting or scavenging compound and a monocyte maturation-promoting agent are co-administered to target a plurality of monocytes to promote monocyte maturation. The monocyte maturation-promoting agent can include Interleukin-1 (IL-1), granulocyte-macrophage colony-stimulating factor (GM-CSF), Interleukin-3 (IL-3), Interleukin-4 (IL-4), Interleukin-6 (IL-6), TNF-α, granulocyte colony-stimulating factor (G-CSF), macrophage colony-stimulating factor (M-CSF), Interleukin-12 (IL-12), Interleukin-15 (IL-15), or Interleukin-18 (IL-18). The monocyte maturation-promoting agent can be administered alone or in combination with a vaccine, a plurality of antigen, or an adjuvant. The ROS inhibiting compound may include histamine and/ or histamine related compounds such as histamine dihydrochloride, histamine phosphate, and histamine receptor agonists. A hydrogen peroxide or ROS scavenging compound such as catalase, glutathione peroxidase or ascorbate peroxidase can also be administered in combination with a monocyte maturation-promoting agent to facilitate the development of monocytes to dendritic cells.

Advantageously, the method of promoting monocyte maturation is accomplished by administering a ROS inhibiting compound and at least one monocyte maturation-promoting agent in vivo. The administration of the monocyte maturation-promoting agent and ROS inhibiting or scavenging compound can be performed simultaneously. Alternatively, the administration of the ROS inhibiting compound may be completed within 24 hours of the administration of the monocyte maturation-promoting agent.

In another aspect of the invention, the ROS inhibitor or scavenger is administered in a dose of from about 0.1 to about 20 mg/day. Preferably, the ROS inhibitor or scavenger is administered in a dose of from about 0.5 to about 8 mg/day. Even more preferably, the amount of ROS inhibitor or scavenger is from about 1 to about 6 mg/day. Advantageously, the monocyte maturation-promoting agent is administered in the dosage of from about 500 to about 1,000,000 U/kg/day; more preferably, the amount is from about 1,000 to about 500,000 U/kg/day; and even more preferably, the amount of monocyte maturation-promoting agent administered is from about 3,000 to about 200,000 U/kg/day.

In another embodiment, a method of augmenting the activity of a monocyte maturation enhancing agent is provided. The method includes administering a ROS inhibitor or scavenger in a pharmaceutically acceptable form and the monocyte maturation enhancing agent, whereby the monocyte maturation effects of the agent are augmented.

Preferably, the monocyte maturation enhancing agent is at least one cytokine. More preferably, the cytokine is Interleukin-1 (IL-1), granulocyte-macrophage colony-stimulating factor (GM-CSF), Interleukin-3 (IL-3), Interleukin-4 (IL-4), Interleukin-6 (IL-6), TNF-α, granulocyte colony-stimulating factor (G-CSF), macrophage colony-stimulating factor (M-CSF), Interleukin-12 (IL-12), Interleukin-15 (IL-15), or Interleukin-18 (IL-18). The monocyte maturation-promoting agent can be administered alone or in combination with a vaccine, a plurality of antigen, or an adjuvant. Most preferably, the cytokine is GM-CSF.

Advantageously, the cytokine is administered in the dosage of from about 500 to about 1,000,000 U/kg/day; more preferably, the amount is from about 1,000 to about 500,000 U/kg/day; and even more preferably, the amount of cytokine administered is from about 3,000 to about 200,000 U/kg/day. The ROS inhibitor or scavenger may be administered in a dose of from about 0.1 to about 10 mg/day. Preferably, the ROS inhibitor or scavenger is administered in a dose of from about 0.5 to about 8 mg/day. Even more preferably, the amount of ROS inhibitor or scavenger is from about 1 to about 5 mg/day.

Another aspect of the disclosed invention further contemplates a method of treating a subject having a neoplastic disease with a ROS inhibitor or scavenger and a monocyte maturation-promoting agent. The method includes identifying a subject having a neoplastic disease, administering a ROS inhibitor or scavenger in a pharmaceutically acceptable form, and simultaneously administering the monocyte maturation-promoting agent. Alternatively, the monocyte maturation-promoting agent can be administered to a subject after a stable concentration of ROS inhibitor or scavenger is achieved. The monocyte maturation-promoting agent may be a cytokine such as IL-1, GM-CSF, IL-3, IL-4, IL-6, TNF-α, G-CSF, M-CSF, IL-12, IL-15, or IL-18. Advantageously, the monocyte maturation-promoting agent is administered in a dose of from about 500 to about 1,000,000 U/kg/day; more preferably, the amount is from about 1,000 to about 500,000 U/kg/day; and even more preferably, the amount of monocyte maturation-promoting agent is administered is from about 3,000 to about 200,000 U/kg/day.

In another embodiment, a method of treating a subject having a chronic infection is provided. The method includes identifying a subject suffering from a chronic infection, administering a ROS inhibitor or scavenger in a pharmaceutically acceptable form, and administering at least one monocyte maturation-promoting agent, wherein the monocyte maturation-promoting agent facilitates the maturation of monocytes to dendritic cells. The monocyte maturation-promoting agent and ROS inhibitor or scavenger can be added simultaneously. Alternatively, the monocyte maturation-promoting agent can be added after a stable concentration of ROS inhibitor or scavenger is achieved. In a preferred embodiment, the monocyte maturation-promoting agent is a cytokine selected from the group consisting of IL-1, GM-CSF, IL-3, IL-4, IL-6, TNF-α, G-CSF, M-CSF, IL-12, IL-15, and IL-18.

The chronic infection can be caused by a virus. The virus can be an adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyomavirus BK, polyomavirus JC, hepatitis C virus, measles virus, rubella virus, human immunodeficiency virus (HIV), human T cell leukemia virus I, or human T cell leukemia virus II.

Alternatively, the chronic infection can be caused by a parasite. The parasite can include species of Leishmania, Toxoplasma, Trypanosoma, Plasmodium, Schistosoma, or Encephalitozoon.

A pharmaceutical composition including a compound effective to promote the maturation of monocytes and a ROS inhibitor or scavenger combined in a single pharmaceutically acceptable carrier is similarly provided. The compound effective to promote the maturation of monocytes may include IL-1, GM-CSF, IL-3, IL-4, IL-6, TNF-α, G-CSF, M-CSF, IL-12, IL-15, or IL-18. Preferably, the compound effective to promote the maturation of monocytes is GM-CSF.

In still another embodiment, a method of manufacture of a pharmaceutical composition including providing a ROS inhibitor or scavenger and at least one monocyte maturation-promoting compound in a pharmaceutically acceptable form is disclosed. Preferably, the monocyte maturation-promoting compound includes IL-1, GM-CSF, IL-3, IL-4, IL-6, TNF-α, G-CSF, M-CSF, IL-12, IL-15, or IL-18. More preferably, the monocyte maturation-promoting compound is GM-CSF.

DETAILED DESCRIPTION OF THE PREFERRED EMBODIMENT

The disclosed invention relates to compositions and methods for augmenting the maturation of monocytes. One or more monocyte maturation-promoting compounds are administered to augment the immune system of a subject suffering from a variety of disease states, including cancer and various infectious diseases. The compositions and methods disclosed herein enhance the maturation of monocytes to dendritic cells, which are some of the most potent antigen presenting cells in the mammalian cellular immune system. The compositions and methods disclosed herein are therefore useful in treating a variety of disease states in which antigen presentation by dendritic cells and subsequent eradication by the host's immune system is involved in the resolution of the disease.

An important mechanism of action for certain cytokines such as granulocyte maturation colony stimulating factor (GM-CSF) is to induce differentiation of monocytes into dendritic cells, which are very efficient antigen-presenting cells. These properties of GM-CSF have been an important background to the use of GM-CSF as an immune adjuvant in the treatment of a variety of disease states, for example, metastatic malignant melanoma. It would be of interest to identify compounds that enhance the rate of monocyte maturation. Additionally, identification of compounds that enhance known monocyte maturation compounds would also be useful in the treatment of various disease states. Known monocyte maturation-promoting compounds include IL-1, IL-3, IL-12, IL-15, IL-18, TNF-α, G-CSF, M-CSF, and GM-CSF. Such compounds induce the expression of cell surface markers characteristic of dendritic cells on monocytes.

CD86 (formerly B7-2) is a cell surface marker for dendritic cells (Kiertscher and Roth, J., *Leukocyte Biol.*, 59:208–218). CD86 is also an important co-stimulatory molecule for the development of cell-mediated immunity (Gieseler et al., *Dev. Immunol.*, 6:25–39 (1998); Slavic et al., *Immunol Res.*, 19:1–24 (1999); Croft et al., *Crit. Rev. Immunol.*, 17:89–118 (1997)). Typically, CD86 on monocytes or other antigen-presenting cells interacts with CD28, an antigen expressed on T-cells (Slavik, J. M. et al., *Immunol. Res.*, 19:1–24 (1999)). This CD28/CD86 interaction provides an activation signal to T-cells and augments and sustains the T-cell activation induced by the interaction of an antigen with the T-cell receptor (McCoy, K. D. et al., *Immunol. Cell Biol.*, 77:1–10).

The disclosed invention is based, in part, on the surprising discovery that compounds that inhibit or scavenge ROS can promote the maturation of monocytes. Histamine protects T-cells and NK-cells against oxidative inhibition induced by monocytes and macrophages. By this mechanism, histamine optimizes lymphocyte activation in response to activating cytokines such as IL-2 or alpha-IFN. In phase III clinical trials, histamine dihydrochloride was administered together with IL-2 to patients with, for example, malignant melanoma. Initial results suggested that the addition of histamine to a regimen of IL-2 therapy significantly improved the survival of melanoma patients with liver metastases.

ROS production and release inhibitors or ROS scavengers enhance the expression of the CD86 antigen on human monocytes in vitro, suggesting that histamine and histamine related compounds facilitate the generation of dendritic cells from monocytes. Accordingly, one embodiment of this invention provides for the administration of ROS production and release inhibitors, and ROS scavengers, to augment the action of certain compounds which promote monocyte maturation. As used herein, "monocyte maturation-promoting agents" include all substances which promote the maturation of monocytes to dendritic cells. Such substances include, without limitation, certain cytokines such as Interleukin-1 (IL-1), granulocyte-macrophage colony stimulating factor (GM-CSF), Interleukin-3 (IL-3), Interleukin-4 (IL-4), Interleukin-6 (IL-6), TNF-$\alpha$, granulocyte colony-stimulating factor (G-CSF), macrophage colony-stimulating factor (M-CSF), Interleukin-12 (IL-12), Interleukin-15 (IL-15), and Interleukin-18 (IL-18).

Compounds that reduce the amount of ROS, when administered alone or in combination with GM-CSF or another monocyte maturation-promoting agent, can act synergistically to stimulate the maturation of monocytes to dendritic cells. Monocyte maturation plays an important role in a host's defenses against arising neoplastic diseases and chronic infections in vivo. Thus, the administration of scavengers of ROS, or compounds which inhibit the production or release of intracellular ROS, alone or in combination with another monocyte maturation-promoting agent, is effective in the treatment of various disease states including, without limitation, cancers and chronic infections, such as those caused by infection by persistent viruses or parasites.

Accordingly, one aspect of the invention involves compositions and methods of enhancing monocyte maturation. In one embodiment, a monocyte maturation-promoting agent is administered in combination with a ROS inhibitor or scavenger. A monocyte maturation-promoting agent is any compound, which facilitates the development and differentiation of monocytes to dendritic cells. Suitable monocyte maturation-promoting agents include, without limitation, IL-1, GM-CSF, IL-3, IL-4, IL-6, TNF-$\alpha$, G-CSF, M-CSF, IL-12, IL-15, and IL-18. Preferably, the monocyte maturation-promoting agent is GM-CSF. ROS production and release inhibitors, as well as ROS scavengers can also be considered monocyte maturation-promoting agents as the administration of these compounds can increase the rate or efficiency of monocyte maturation.

Histamine or other ROS inhibitors or scavengers are administered alone or in combination with at least one other monocyte maturation-promoting agent to enhance monocyte maturation. The term "histamine" as used herein incorporates ROS inhibiting agents as well as ROS scavengers including a variety of histamine and histamine-related compounds. For example, histamine, the dihydrochloride salt form of histamine (histamine dihydrochloride), histamine phosphate, other histamine salts, histamine esters, or histamine prodrugs, and histamine receptor agonists are encompassed by the term "histamine." The administration of compounds that induce the release of endogenous histamine from a patient's own tissue stores are also included within the scope of the definition of the term "histamine" as used herein. Such compounds include IL-3, retinoids, 9-cis-retinoic acid, all-trans-retinoic acid, and allergens. Other ROS production and release inhibitory compounds such as NADPH oxidase inhibitors like diphenlyeneiodonium are within the scope of the disclosed invention and included within the definition of the term "histamine" as used herein. Similarly, serotonin and 5HT agonists are included in the definition of "histamine" as used herein.

The methods and compositions of the disclosed invention further contemplate the administration of scavengers of ROS in concert with monocyte maturation-promoting agents to facilitate the development of monocytes to dendritic cells, thereby enhancing antigen presentation and subsequent eradication of certain target cells. Known scavengers of ROS include the enzymes catalase, glutathione peroxidase and ascorbate peroxidase. Additionally, vitamins A, E, and C are known to have scavenger activity. Minerals such as selenium and manganese can also be efficacious compounds for scavenging ROS. It is intended that the disclosed invention include the administration of the compounds listed and those compounds with similar ROS inhibitor activity.

Histamine or a histamine-related compound and a monocyte maturation-promoting agent may be administered alone to enhance monocyte maturation or in combination with a plurality of drugs, vaccines, antigens, or adjuvants to provide an effective treatment for a variety of disease states.

Administration of Monocyte Maturation-Promoting Agents

The administration of one or more monocyte maturation-promoting agents to enhance the development of monocytes to dendritic cells, together with the inhibiting or scavenging compounds discussed above, can be accomplished in vitro or in vivo by any of a number of methods well known to those of skill in the art. When administering the compositions of the disclosed invention in vivo, suitable delivery methods include parenteral delivery through intravenous, intraperitoneal, or intramuscular injection. The monocyte maturation-promoting agent and the ROS scavenger can be administered separately or as a single composition. When administered separately, it is contemplated that the monocyte maturation-promoting agent is administered either first or last.

The compounds disclosed herein can be administered in water with or without a surfactant such as hydroxypropyl cellulose. Dispersions are also contemplated, such as those utilizing glycerol, liquid polyethylene glycols, and oils. Antimicrobial compounds can also be added to the preparations. Injectable preparations can include sterile aqueous solutions or dispersions and powders that can be diluted or suspended in a sterile environment prior to use. Carriers such as solvents or dispersion media contain water, ethanol polyols, vegetable oils and the like can also be added to the compounds described herein. Coatings such as lecithins and surfactants can be used to maintain the proper fluidity of the composition. Isotonic agents such as sugars or sodium chloride can be added, as well as products intended to delay absorption of the active compounds such as aluminum monostearate and gelatin. Sterile injectable solutions are prepared according to methods well known to those of skill in the art and can be filtered prior to storage and/or use. Sterile powders can be vacuum or freeze dried from a solution or suspension. Sustained-release preparations and formulations are also contemplated by the present invention. Any material used in the composition of the present invention should be pharmaceutically acceptable and substantially non-toxic in the amounts employed.

All preparations can be provided in dosage unit forms for uniform dosage and ease of administration. Each dosage unit form contains a predetermined quantity of active ingredient calculated to produce a desired effect in association with an amount of pharmaceutically acceptable carrier.

It should be understood that the compounds can be administered as a single dose or, more preferably, for prolonged periods of time. Typically, the treatment can be administered for periods up to about one week, one month, and even for periods longer than one year. In one embodiment, the treatment can be administered for up to three years or longer. In some instances, the treatment may be discontinued and then resumed at a later time. A daily dose can be administered as a single dose, or it can be divided into several doses, especially if negative side effects are observed. In addition, the compounds can be administered as a single composition, or separately. If administered separately, the compounds should be given on the same day, such that the activation of the monocyte maturation-promoting agent is enhanced.

Preferred dosage range can be determined using techniques known to those having ordinary skill in the art. Monocyte maturation-promoting agents can be administered in an amount of from about 500 to about 1,000,000 U/kg/day; more preferably, the amount is from about 1,000 to about 500,000 U/kg/day, and even more preferably, the amount is from about 3,000 to about 200,000 U/kg/day. One of skill in the art will appreciate that, in each case, the dose of the monocyte maturation-promoting agent depends on the activity of the administered compound.

Compounds which inhibit the release or formation of intracellular ROS, or scavengers of ROS, can be administered in an amount of from about 0.1 to about 20 mg/day. Preferably, the amount is from about 0.5 to about 8 mg/day. Even more preferably, the amount of ROS inhibitor or scavenger is from about 1 to about 6 mg/day. However, in each case, the dose depends on the activity of the administered compound. Appropriate doses for any particular host can be readily determined by empirical techniques well known to those of ordinary skill in the art.

A method of treating patients with cancer or chronic infections with the combination of a monocyte maturation-promoting compound and a ROS inhibitor or scavenger is described. Cancers are caused by the progressive, unregulated growth of the progeny of a single abnormal cell. The term "cancer" as used herein includes neoplastic diseases, neoplastic cells, tumors, tumor cells, malignancies and any transformed cell, including both solid tumors and diffuse neoplastic disease. Historically, cancer cells generally have been thought to escape detection and destruction by the immune system because cancer cells contain the same genetic material as other non-cancerous cells of the body. The genetic identity or similarity of cancer cells and healthy cells in the body supposedly causes the difficulty of distinguishing cancer cells from normal cells, and the immune system is therefore unable to mount an effective immune response, as evidenced by the persistence of cancer cells in the body.

To the contrary, a variety of tumor associated antigens (TuAAs) have been described which could, and indeed do, provoke immune responses. Numerous studies have described tumor infiltrating lymphocytes which can kill target cells presenting peptides derived from various TuAAs in vitro. In some embodiments, the compositions of the disclosed invention are administered to a subject to treat cancer. The administration of a known monocyte maturation-promoting agent in combination with histamine or histamine related compounds results in the facilitation of the maturation of monocytes to dendritic cells. As a result, more antigen presenting cells present TuAAs to cytotoxic T-lymphocytes. Cytotoxic T-lymphocytes can then specifically attack and kill tumor cells. Thus, increasing the number of dendritic cells capable of presenting TuAAs on their cell surfaces would be a boon to the treatment of cancers.

In one embodiment, at least one monocyte maturation-promoting agent in a pharmaceutically acceptable form is administered to a subject presenting with a cancer. In some embodiments, a ROS inhibitor or scavenger and an additional monocyte maturation-promoting agent, both in a pharmaceutically acceptable form, are likewise administered. The monocyte maturation-promoting agent and the ROS inhibitor or scavenger can be administered separately or as a single composition. Advantageously, multiple monocyte maturation-promoting agents are administered in concert with a ROS inhibiting or scavenging agent. When administered separately, it is contemplated that the at least one monocyte maturation-promoting agent is administered either first or last. Suitable monocyte maturation-promoting agents include IL-1, GM-CSF, IL-3, IL-4, IL-6, TNF-α, G-CSF, M-CSF, IL-12, IL-15, and IL-18. Preferably, the monocyte maturation-promoting agent is GM-CSF.

The method described herein may be utilized alone or in combination with other anti-cancer therapies, as determined by the practitioner. For example, the co-administration of a ROS inhibiting agent or ROS scavenging agent and at least one monocyte maturation-promoting agent with a cancer vaccine, adjuvant and/or anti-cancer drug is specifically contemplated.

A method of treating chronic infections is similarly contemplated. Chronic infections often result from infection by pathogens that are able to escape detection and subsequent eradication by the host's immune system. Examples of such pathogens include, but are not limited to certain viruses, protozoa, or other organisms.

A wide variety of mechanisms are employed by persistent pathogens in order to establish chronic infections in the host organism. A common hallmark is reduced or altered antigen expression. Viral antigen presentation begins with the digestion of viral antigens into peptides by the proteasome. After the proteasome digests the protein into peptides, some of the peptides are loaded onto the class I complex in the endoplasmic reticulum and transported to the cell surface. At the cell surface, the class I-peptide complex is recognized by T cell receptors on the surface of cytotoxic T-lymphocytes and the infected cells are killed.

Certain viruses and other intracellular parasites may escape T cell recognition by down-regulating the expression of host molecules necessary for efficient T cell recognition of infected cells. Chronic infections such as those caused by adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyomavirus BK, polyomavirus JC, hepatitis C virus, measles virus, rubella virus, human immunodeficiency virus (HIV), human T cell leukemia virus I, and human T cell leukemia virus II persist in the host because the host is unable to mount a sufficient cytotoxic T-cell response against these viruses. Similarly, numerous parasites such as species of Leishmania, Toxoplasma, Trypanosoma, Plasmodium, Schistosoma, or Encephalitozoon persist in the host. Without being limited to a particular theory, it is hypothesized that such persistence may be attributed to an unsatisfactory recognition and subsequent resolution of the pathogens by the host's immune system, namely, the cytotoxic T-lymphocytes fail to identify and kill the infected target cells. An alternative explanation is that when macrophages are making ROS, the macrophages are unable to present antigen because the ROS would kill T-cells. Histamine and histamine related compounds may serve as a switch, wherein the amount of ROS is decreased. Consequently, an increase of CD86 is observed on the surface of the dendritic cells, heralding an increase in antigen presentation by the dendritic cells.

As described herein, and previously unrecognized in the art, it is possible to increase the rate and number of monocytes that mature into dendritic cells by administering a maturation promoting compound, such as histamine, to a subject in need thereof. This administration serves to increase viral antigen presentation by antigen presenting cells. By facilitating the development of monocytes to dendritic cells for antigen presentation, more antigen presenting cells will display antigens associated with chronic viral infections on their cell surfaces. Receptors on cytotoxic T-lymphocytes will bind to the antigens displayed on the surface of the antigen presenting cells and, as a result, the chronically infected cells will be killed by the cytotoxic T-lymphocytes.

Accordingly, a method of treating a subject having a chronic infection is disclosed. The chronic infection may be caused by a virus or a parasite such as the species described above. After a subject presenting with a chronic infection is identified, the subject is administered a ROS inhibitor or scavenger such as histamine or a histamine related compound in a pharmaceutically acceptable form. In one embodiment, at least one monocyte maturation-promoting agent is also administered to the subject in a pharmaceutically acceptable form. In another embodiment, a plurality of monocyte maturation-promoting agents are administered. The at least one monocyte maturation-promoting agent and the ROS inhibitor or scavenger can be administered separately or as a single composition. When administered separately, it is contemplated that the monocyte maturation-promoting agent is administered either first or last. Suitable monocyte maturation-promoting agents include IL-1, GM-CSF, IL-3, IL-4, IL-6, TNF-α, G-CSF, M-CSF, IL-12, IL-15, and IL-18. Preferably, the monocyte maturation-promoting agent is GM-CSF. The method of treating chronic infections as described above can be utilized alone or in combination with other anti-viral or anti-parasitic therapy regimes as determined by a skilled practitioner. For example, the administration of a monocyte maturation-promoting agent and a ROS inhibitor or scavenger can be accompanied by the administration of an anti-viral vaccine or various adjuvants known by one of skill in the art to stimulate a subject's immune system.

The following examples teach the methods and compositions disclosed herein for promoting the maturation of monocytes to dendritic cells through the administration of a ROS inhibitor or scavenger in concert with a monocyte maturation-promoting agent. These examples are illustrative only and are not intended to limit the scope of the invention disclosed herein. The treatment methods described below can be optimized using empirical techniques well known to those of ordinary skill in the art. Moreover, artisans of skill would be able to use the teachings described in the following examples to practice the full scope of the invention disclosed herein.

EXAMPLE 1

Treatment of Monocytes with Histamine and GM-CSF

Separation of Monocytes. Peripheral venous blood was obtained as freshly prepared leukopacks from four healthy blood donors at the Blood Centre, Sahlgren's Hospital, Göteborg, Sweden. The blood (65 ml) was mixed with 92.5 ml Iscove's medium, 35 ml 6% Dextran (Pharmacia, Uppsala, Sweden) and 7.5 ml ACD (Baxter, Deerfield, Ill.). After incubation for 15 min at room temperature, the supernatant was carefully layered onto Ficoll-Hypaque (Lymphoprep, Nyegaard, Norway). Mononuclear cells were collected at the interface after centrifugation at 380 g for 15 min and washed twice in PBS followed by resuspension in Iscove's medium with 10% human AB+serum.

The mononuclear cells were further enriched for monocytes using the counter-current centrifugal elutriation (CCE) technique as described in detail in Hellstrand, K. et al., *J. Immunol.*, 153:4940–4947 (1994). Briefly, the mononuclear cells were resuspended in elutriation buffer containing 0.05% BSA and 0.015% EDTA in buffered NaCl and fed into a Beckman J2-21 ultracentrifuge with a JE-6B rotor at 2100 rpm. A fraction with >90% monocytes (as reflected by their expression of the CD14 antigen) was obtained at a flow rate of 18 ml/min.

Treatment and Cell Staining. The monocytes ($3\times10^5$ cells/ml in a total volume of 1 ml) were incubated in 24-well microplates at 37° C. overnight (16 hrs). During incubation, the monocytes were treated with histamine dihydrochloride (purchased from Sigma, St. Louis, USA) at a final concentration of 10 $\mu$M and/or GM-CSF (Leukomax®, Schering Plough, Stockholm, Sweden) at a final concentration of 0.15 $\mu$g/ml. After the completion of incubation, cells were centrifuged, and monoclonal antibodies to CD14 (a pan-monocyte-antigen) or CD86 (a dendritic cell marker) (purchased from Becton Dickinson, Stockholm, Sweden) were added to the pellet for staining, as described in Hellstrand, K. et al., *J. Immunol* 153:4940–4947 (1994). After washing, the cells were analyzed for cell surface expression of CD14 and CD86.

Results

A mean of 88% of the monocytes expressed CD86 after overnight incubation with GM-CSF. The corresponding Figure for monocytes treated with GM-CSF+histamine was 97%.

Histamine potentiated the up-regulation of CD86 antigen expression intensity induced by GM-CSF. Specifically, the intensity of cell surface expression of CD86 (a reflection of how many CD86 molecules are expressed on each cell) was moderately enhanced by histamine treatment, and the combination of histamine+GM-CSF yielded a higher expression of CD86 than did treatment either with histamine alone or with GM-CSF alone (Table 1, below). The expression of CD86 on monocytes treated with histamine+GM-CSF was higher than that of monocytes treated with GM-CSF alone in all experiments. The median cell surface expression of CD86 in monocytes treated with histamine+GM-CSF was 352% (mean)/366% (median) of that of corresponding monocytes treated with GM-CSF alone.

TABLE 1

Intensity of the CD86 Antigen on Human Monocytes After Treatment With Histamine and/or GM-CSF

| | GM-CSF | | histamine + GM-CSF | |
|---|---|---|---|---|
| exp. no. | geometric mean | Median | geometric mean | median |
| 1 | 186 | 235 | 332 | 483 |
| 2 | 89 | 78 | 280 | 264 |
| 3 | 120 | 173 | 413 | 685 |
| 4 | 109 | 120 | 448 | 562 |

The cell surface expression of CD14 was similar in monocytes treated with GM-CSF and in monocytes treated with GM-CSF+histamine, suggesting that the enhancement of CD86 expression by histamine+GM-CSF was not the result of non-specific enhancement of antibody uptake.

It was found that histamine enhances the GM-CSF-induced expression of the CD86 co-stimulatory molecule on human monocytes. Histamine up-regulated monocytes HLA-DR expression, which is characteristically high on dendritic cells. The administration of histamine in concert with a monocyte maturation-promoting agent such as GM-CSF augmented the activity of the monocyte maturation-promoting agent. The co-administration of histamine with GM-CSF resulted in an appreciable increase in CD86, a cell surface marker for dendritic cells. Moreover, histamine induced up-regulation of important co-stimulatory molecules on monocytes and macrophages. Histamine enhances the effect of GM-CSF on the maturation of monocytes to dendritic cells. The administration of histamine has significant relevance to adaptive immunity by facilitating the development of professional antigen-presenting dendritic cells from monocytes.

EXAMPLE 2

Administration of Histamine Dihydrochloride to Protect NK Cells, T Cells, and NK Lymphocytes Against Oxidatively Induced Apoptosis Oxidative stress, i.e. toxicity inflicted by reactive oxygen species (ROS), has been proposed to contribute to the state of immunosuppression at the site of malignant tumors and in chronic viral infections. Lymphocytes residing within or adjacent to tumors display signs of oxidative damage, including a higher degree of apoptosis and a defective transmembraneous signal transduction. The oxidative stress at the site of tumor growth is presumable conveyed by ROS produced by adjacent phagocytic cells such as monocyte/macrophages (MO) or neutrophilic grangulocytes (GR). Histamine, an inhibitor of ROS production in phagocytes, is currently used as an adjunct to lymphocyte activating cytokines such as IL-2 and IFN-α with the aim to enhance cytokine efficiency. Results from clinical trials suggest that patients with liver melanoma metastasis and patients with chronic hepatitis C benefit from histamine treatment, suggesting that histamine may be selectively effective in liver tissue.

In human liver, NK-cells as well as NK/T-cells are much more abundant than in peripheral blood. Therefore, the sensitivity of three types of human lymphocytes, CD3+ T cells, CD3−/56+ NK cells, and CD3+/56+ NK/T cells, was compared to oxidatively induced apoptosis in vitro. All three cell types became apoptotic after incubation with autologous MO or GR or after treatment with hydrogen peroxide, a reactive species of oxygen. Thus, at a lymphocyte to MO ratio of 1:1, 35±5% of NK-cells, and 76±7% of NK/T-cells became apoptotic. Corresponding frequencies of apoptosis at a lymphocyte to GR ratio of 1:1 were 21±4% (T cells), 30±7% (NK cells), and 66±8% (NK/T cells). All data are the mean±s.e.m. (n=15–30 blood donors). Apoptosis in all cell types was significantly prevented by histamine (p<0.001). The higher sensitivity to oxidatively induced apoptosis in NK/T cells and NK cells was confirmed in experiments in which apoptosis was induced by exogenous hydrogen peroxide; at 25 $\mu$M of hydrogen peroxide, 35±5% of T cells, 65±7% of NK cells, and 78±7% of NK/T cells (n=8) became apoptotic. We concluded that liver-type lymphocytes, in particular NK/T cells, are particularly sensitive to oxidative stress. Therefore, it is proposed that anti-oxidative agents such as histamine may be more effective in liver neoplasia or chronic infection as the result of a higher sensitivity to oxidatively induced apoptosis in liver-infiltrating lymphocytes.

Treatment of Chronic Viral Infections

Successful resolution of an infection by a virus or other intracellular parasite requires that the host's immune system recognize the infected cells as "non-self" and to mount a sufficient response to inhibit the growth and dissemination of the infective agent. Because viruses infect the host's own cells, recognition and subsequent destruction of infected cells can be difficult. Several viruses and intracellular parasites persist in the host because the host's immune system fails to distinguish infected cells as "non-self" and thus is incapable of mounting an effective cytotoxic T cell response directed against the infected cells. The compositions and methods of the invention disclosed herein can be employed to treat chronic viral infections. The co-administration of a ROS inhibitor or scavenger with a monocyte maturation-promoting agent will result in an increased immune response to a viral infection.

EXAMPLE 3

Treatment of Herpes Genitalis

The herpesviridae family of viruses, for example, contains some of the most important human pathogens known. Herpes infections are recurrent and extremely painful. The level of discomfort may be attributed to the fact that the herpes virus lies dormant in the trigeminal ganglion of the subject and then passes through the nerves to the skin surface during an outbreak.

A female subject suffering from herpes genitalis is administered a cream containing histamine phosphate in a concentration of 0.7% by weight of the formulation and GM-CSF in a concentration of 0.15% by weight of the formulation. Using an applicator, the cream is injected into the vaginal space to treat herpetic lesions therein. The cream is applied three times a day for a period of five days. The composition acts to enhance the maturation of monocytes, thereby allowing the subject's immune system to attack virally-infected cells. There are no untoward reactions and the treatment eradicates the viral infection.

EXAMPLE 4

Treatment of Chicken Pox

A vaccine comprising attenuated chickenpox virus, 0.025% GM-CSF by weight of the vaccine, and 1.0% histamine by weight of the vaccine is formulated for parenteral administration to a subject. The histamine acts to augment the activity of GM-CSF as a monocyte maturation-promoting agent. An immune response is mounted by the subject against the chickenpox virus.

EXAMPLE 5

Treatment of HIV

A subject presenting with HIV infection is administered intravenously a composition comprising an effective dose of a protease inhibitor, a histamine receptor agonist in a pharmaceutically acceptable form, and G-CSF in a pharmaceutically effective form. The composition acts to enhance the maturation of monocytes, thereby allowing the subject's immune system to attack virally infected cells. An increase in the number of dendritic cells presenting HIV antigen is observed. The histamine receptor agonist enhances the maturation of monocytes to dendritic cells.

Treatment of Chronic Parasitic Infections

Examples of pathogens which persevere in the host as chronic infections include protozoa such as Leishmania, Toxoplasma, Trypanosoma, Plasmodium (the causative agent of malaria), Schistosoma, and Encephalitozoon. Such organisms pose significant health risks throughout the world. Malaria, for example, is an internationally devastating disease which infects over 400 million people and kills three million people per year.

EXAMPLE 6

Treatment of Malaria Infection

A subject presenting with malaria is parenterally administered GM-CSF at a rate of 100,000 U/kg/day and serotonin at a dosage of 6 mg/day. The composition acts to enhance monocyte maturation, thereby allowing the subject's immune system to eradicate cells infected with Plasmodia species. Specifically, serotonin enhances the monocyte maturation-promoting activity of G-CSF. An increase in the number of dendritic cells presenting antigens associated with Plasmodia is observed. T-cells recognize the Plasmodia antigens as foreign, attack, and kill the cells. The number of infected cells decreases.

Treatment of Cancer

Each year, the number of diagnosed cancer cases is approximately 1.5 million in the United States and over 5 million worldwide. Cancers such as leukemia, carcinoma, lymphoma, astrocytoma, sarcoma, glioma, retinoblastoma, melanoma, Wilm's tumor, bladder cancer, breast cancer, colon cancer, pancreatic cancer, prostate cancer, lung cancer, liver cancer, stomach cancer, cervical cancer, testicular cancer, renal cell cancer, and brain cancer pose significant health risks and if left untreated, may result in death.

A myriad of treatment options are available for patients with cancer including surgical excision, chemotherapy, radiotherapy, and bone marrow transplantation. While many conventional cancer therapies are often effective in thwarting neoplastic growth, normal cells are frequently compromised. Consequently, numerous side effects are attendant to conventional cancer therapies.

Recent efforts in the battle against cancer have focused on enlisting the immune system of the patient to eradicate neoplastic cells displaying tumor associated antigens to avoid the side effects associated with conventional cancer therapies. The facilitation of the maturation of monocytes to antigen presenting dendritic cells enhances a host's immune response against tumor cells.

Histamine and histamine related compounds such as histamine dihydrochloride have been shown to protect T cells and NK cells against oxidative inhibition induced by monocytes (specifically, by macrophages). By this mechanism, histamine optimizes lymphocyte activation in response to activating cytokines such as IL-2 or IFN-α. In ongoing clinical trials, histamine dihydrochloride has been administered in combination with IL-2 alone or in combination with IFN-α to patients with metastatic melanoma, renal cell carcinoma, acute myelogenous leukemia, and hepatitis C. The results suggest that the addition of histamine to a regimen of IL-2 significantly improves the survival of melanoma patients with liver metastases. GM-CSF induces the differentiation of monocytes into dendritic cells, which are effective antigen presenting cells. These properties of GM-CSF have been an important background to the use of GM-CSF as an immune adjuvant in metastatic melanoma.

EXAMPLE 7

Treatment of Metastatic Melanoma

A female subject presenting with metastatic melanoma of the liver is administered 200,000 U/kg/day of G-CSF and histamine phosphate at a dose of 10 mg/day. The administered agents act to enhance the maturation of monocytes, thereby enabling the subject's immune system to attack the cancerous cells in the liver. A decrease in tumor mass is observed.

EXAMPLE 8

Treatment of Prostate Cancer

A male subject presenting with prostate cancer is administered 300,000 U/kg/day of GM-CSF, 100,000 U/kg/day of IL-12, and histamine dihydrochloride at a dose of 4 mg/day. The administered agents act to enhance the maturation of monocytes, thereby enabling the subject's immune system to attack the neoplastic cells. A decrease in tumor mass is observed.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. An in vivo method of promoting the maturation of monocytes into dendritic cells comprising administering to a subject a monocyte maturation-promoting agent selected from the group consisting of GM-CSF, IL-4, IL-6, TNF-α, G-CSF, M-CSF, and IL-18, and a ROS production or release inhibitor selected from the group consisting of histamine, histamine salts, histamine esters, histamine receptor agonists, serotonin, 5HT agonists, and an endogenous histamine releasing compound.

2. The method of claim 1, wherein the administration of said ROS production or release inhibitor and said monocyte maturation-promoting agent is performed simultaneously.

3. The method of claim 1, wherein the administration of said ROS production or release inhibitor is performed within 24 hours of the administration of said monocyte maturation-promoting agent.

4. The method of claim 1, wherein said monocyte maturation-promoting agent is administered in a dose of from about 500 to about 1,000,000 units per kilogram of body weight per day.

5. The method of claim 1, wherein said monocyte maturation-promoting agent is administered in a dose of from about 3,000 to about 200,000 units per kilogram of body weight per day.

6. The method of claim 1, wherein said ROS production or release inhibitor is administered in a dose of from about 0.1 to about 20 mg/day.

7. The method of claim 1, further comprising administering a ROS scavenger selected from the group consisting of catalase, glutathione peroxidase, ascorbate peroxidase, vitamin A, vitamin E, and vitamin C.

8. The method of claim 1, wherein said ROS production or release inhibitor and said monocyte maturation-promoting agent are administered over a period of time between about one week to one year.

9. The method of claim 1, wherein said ROS production or release inhibitor and said monocyte maturation-promoting agent are administered parenterally.

* * * * *